Figure 1A:
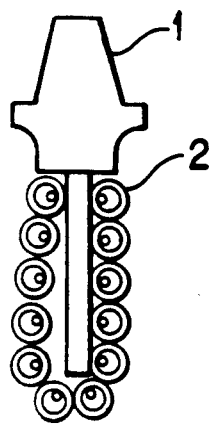

United States Patent [19]

Kurze et al.

[11] Patent Number: 5,032,129
[45] Date of Patent: Jul. 16, 1991

[54] ACTIVE IMPLANT

[75] Inventors: Peter Kurze, Oberlichtenau; Waldemar Krysmann, Karl-Marx-Stadt; Wolfram Knoefler; Hans-Ludwig Graf, both of Leipzig; Wolfgang Bethmann, Dessau; Horst Hampel, Feipzig, all of German Democratic Rep.

[73] Assignee: Technische Hochschule Karl-Marx-Stadt, Chemnitz, German Democratic Rep.

[21] Appl. No.: 932,748

[22] Filed: Nov. 18, 1986

[30] Foreign Application Priority Data

Dec. 5, 1985 [DD] German Democratic Rep. ... 283775

[51] Int. Cl.$^5$ .............................................. A61F 2/28
[52] U.S. Cl. ....................................... 623/16; 623/23; 433/201.1
[58] Field of Search ............... 623/16; 433/201.1, 173; 427/2

[56] References Cited

U.S. PATENT DOCUMENTS

| | | |
|---|---|---|
| 3,906,550 | 9/1975. | Rostoker et al. . |
| 4,038,705 | 8/1977 | Owens et al. . |
| 4,326,305 | 4/1982 | Davidas ............................ 623/16 |
| 4,495,664 | 1/1985 | Blanquaert ........................ 623/23 |

FOREIGN PATENT DOCUMENTS

| | | |
|---|---|---|
| 2628485 | 1/1977 | Fed. Rep. of Germany . |
| 2733394 | 2/1977 | Fed. Rep. of Germany . |
| 2754917 | 6/1979 | Fed. Rep. of Germany . |
| 133518 | 12/1977 | German Democratic Rep. . |
| 156312 | 9/1980 | German Democratic Rep. . |
| 156462 | 9/1980 | German Democratic Rep. . |

OTHER PUBLICATIONS

H. R. Muehlemann, Schweiz. Mschr. Zahnheilk. 85 (1975) pp. 97–112.
M. Hodosh et al., J. Pros. Dent. 24 (1970) pp. 453–460.
L. J. Peterson et al., J. Dent. Res. 59 (1980) pp. 99–108.
F. Huber, Applied Physics Letters 2 (1963) pp. 76 and 78.
C. A. L. Bassett et al., Nature 204 (1964) pp. 652–654.

Primary Examiner—Randall L. Green
Attorney, Agent, or Firm—Jordan and Hamburg

[57] ABSTRACT

The active implant for use in medicine, such as for tooth implants or endoprosthesis For positions influencing the growth mechanisms of the bone and which remain in place for a long time. The active implant comprises a base and flexible structures therein provided with an oxide which contains growth stimulators and has a stable p-n junction.

3 Claims, 1 Drawing Sheet

U.S. Patent     July 16, 1991     5,032,129

ACTIVE IMPLANT

FIELD OF APPLICATION OF THE INVENTION

The invention relates to an active implant for medical use, in particular as a tooth implant or endoprosthesis, as well as in veterinary medicine.

CHARACTERISTICS OF THE KNOWN TECHNICAL SOLUTIONS

In the development of implants, in particular dental implants, it has been proved that porous implants are better incorporated by the bone than smooth and flat shapes (Muehlemann/Schweiz. Mschr. Zahnheilk. 85 (1975) 97–112/, Hodosh et al./J. Prothet. Dent. 24 (1970) 453–460/, Peterson et al./J. Dent. Res. 59 (1980) 99–108/). It is known that this principle requires sintering pressed wires (U.S. Pat. No. 3,906,550). Controlled porosities are also attained by sintering wire spirals onto substrata (U.S. Pat. No. 4,038,705). Surface roughnesses are created by spraying layers of titanium (DE-OS 26 28 485) and by porous ceramic (DE-OS 27 54 917, DE-OS 27 33 394).

A disadvantage of the sintering method with wire spirals and pressed wires is that it almost completely inhibits the bending-deformability of the material.

Furthermore, it is known that layers of carbon, polymers and ceramic improve the biocharacteristics of metals by counteracting corrosion and/or by inducing bioactive processes. Layers of mica polymers (DD-WP 156 462), phthalocyanines (DD-WP 156 312) and other polymers (DD-WP 133 518) serve the same purpose.

A disadvantage of these implants, on the one hand, is the partially low adhesion force of the layer and, on the other hand, the inhibition of electrical activities of the implant materials. Furthermore, all methods require high technical expense. It is furthermore known that bone growth can be stimulated by flowing current (Bassett, Pawluk and Becker/Nature 204 (1964) 652–654/, Cieszynski/Arch. Immunol. Exp. Thei. 11 (1963) 199–215/).

During mechanical shaping, metal-metal oxide junctions of particular metals, for example, titanium, also generate electrical potentials which, however, cannot be taken advantage of and applied in current-stimulating implants (Huber/Applied Physics Letters 2 (1963) 76–78/).

OBJECT OF THE INVENTION

The object of the invention is to provide an active implant which remains permanently in the bone and stimulates the growth mechanisms of the bone.

EXPLANATION OF THE NATURE OF THE INVENTION

It is the object of the invention to provide implants which positively influence the growth mechanisms of the bone, remain in place for a long period and overcome the above indicated disadvantages. According to the invention the object is solved by providing an active implant comprised of bendable metal structures and/or ceramic structures, wire structures or foil structures, with an oxide containing growth stimulator, or consisting thereof, and having a stable p-n junction. These growth stimulators are piezoelectrically active substances, such as, menely for example, dihydrogen phosphates, zirconates, tartrates, titanates, tourmalines and quartz.

Deformation potentials are generated due to the combination of the inherent elasticities of the materials such as metals, metal alloys and ceramics and the piezoelectric behavior of particular metal-metal oxide junctions or compositions, preferably of the elements Al, Ti, Ta, Zr, Zb, Hf, among others. The solution according to the invention for the development of active implants, in particular of bendable metal structures and/or ceramic structures, comprises providing surface-structured, especially delicate tooth implants or massive endoprostheses wrapped with thin wire and/or foil made of Ti- and/or Ra- and/or Nb- and/or Al- and/or Zr- and/or Hf, or comprised thereof, and providing the implants with a significant oxide which contains growth stimulators such as potassium and/or ammonium dihydrogen phosphates and/or zirconates and/or tourmalines and/or quartzes and/or titanates, etc. According to the invention, the even formation of the oxide layer and creation of a stable p-n junction on the flexible structures, wire or foil structures or on portions thereof with simultaneous doping of the oxide with growth stimulators occurs in particular with the help of the anodic oxidation method under spark discharge. With the help of this method of layer formation, even thin wires or foils are sintered onto the base body of the implant and are locally fixed.

The flexible structures with their stable p-n junctions are of such dimensions that the acting thereon forces, depending on the location of the implant, lead to a reversible deformation of these structures, that deformation potentials are generated and bone growth and tissue growth are permanently stimulated by the resultant flow of stimulus current.

EXAMPLE

Figure 1B:
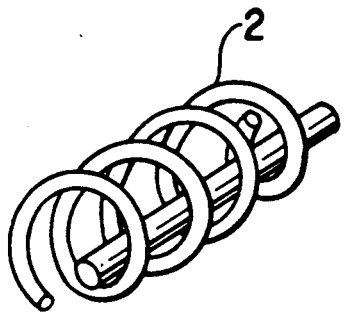
Figure 1C:
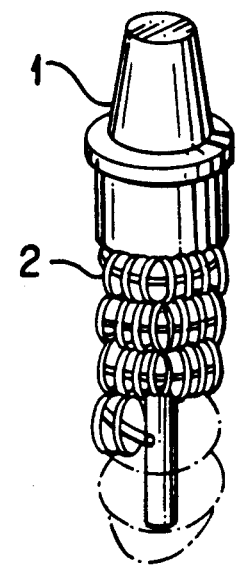
Figure 2A:
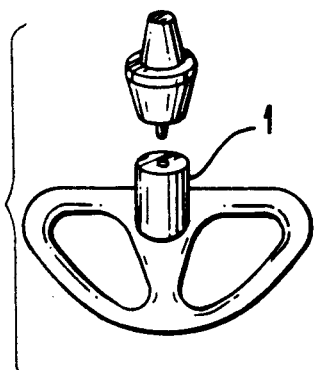
Figure 2B:
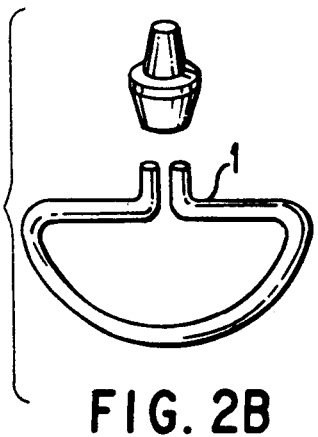
Figure 2C:
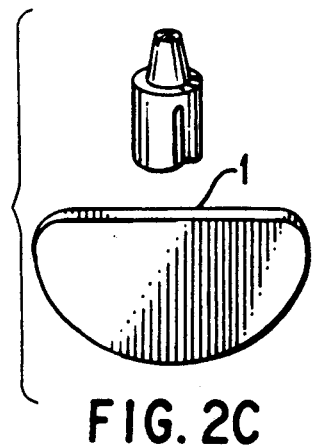
Figure 2D:
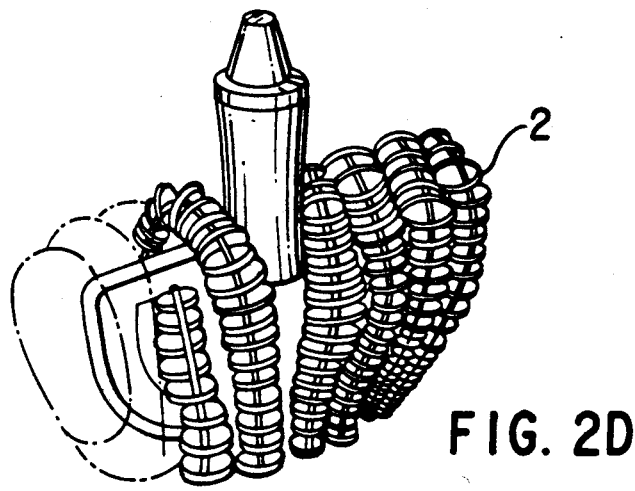

The invention will be explained in greater detail with reference to the accompanying drawings, which show:

FIG. 1: a single tooth implant—(a) longitudinal view, (b) bendable spiral wire construction, (c) perspective drawing; and FIG. 2: an implant with extensions—(a) cast base, (b) base made of wire construction, (c) base made of sheet metal, (d) perspective drawing of the implant with extensions.

A flexible structure 2 comprised a titanium wire spiral is arranged on the base 1 made of titanium. Subsequently, in order to apply the oxide, this implant is subjected to an anodic oxidation under spark discharge in an electrolyte comprised of 0.6 molar fluoride, 0.5 molar dihydrogen phosphate, 0.1 molar tetraborate, 0.1 molar ammonium and 1.2 molar sodium and 10 g barium titanate per liter of solution, at 130 V and 1 A. The oxidized titanium wire spiral thereby sinters fixedly onto the oxidized base 1 and the thereby resulting significantly roughened oxide layer contains growth stimulators of the electrolyte. The titanium wire spiral coated in this way has piezoelectrical behavior both in the stressed and unstressed state, i.e., a deformation potential is generated with resulting flow of stimulus current. Tests have shown that bone formation is especially well developed around the wire spiral. This is attributed to the stimulus current which is guaranteed by the implant functioning for a long time. The intensity of the bone contact is approximately 15% higher than in case of untreated titanium.

We claim:

1. An active medical implant, comprising:
   a base body; and
   means exhibiting piezoelectric behavior in both stressed and unstressed states to generate a deformation potential resulting in the flow of stimulus current in said implant for permanent stimulation of bone and tissue growth, said means comprising
   a flexible structure having a stable p-n junction made of a material selected from the group consisting of metal, ceramic, wire, foil and mixtures thereof, and
   an oxide layer on said base body and flexible structure, said oxide layer containing piezoelectrically active growth stimulators and being derived from said base body and flexible structure by anodic oxidation of said base body and flexible structure under spark discharge in an electrolyte, said flexible structure being sintered to said base body as a result of said anodic oxidation.

2. An implant as in claim 1, wherein said base body and flexible structure are selected from the group consisting of Ti, Ta, Nb, Al, Zr, Hf and mixtures thereof.

3. An implant as in claim 1, wherein said growth stimulators are selected from the group consisting of dihydrogen phosphates, zirconates, tartrates, titanates, tourmalines, quartzes and mixtures thereof.

* * * * *